United States Patent
Lockwood

(10) Patent No.: US 9,566,305 B2
(45) Date of Patent: Feb. 14, 2017

(54) THERAPEUTIC COMPOSITIONS AND METHODS FOR ADDRESSING PHYSIOLOGICAL STRESSES AND AGING

(71) Applicant: 4Life Patents, LLC, Sandy, UT (US)

(72) Inventor: Christopher M. Lockwood, Draper, UT (US)

(73) Assignee: 4LIFE PATENTS, LLC, Sandy, UT (US)

( * ) Notice: Subject to any disclaimer, the term of this patent is extended or adjusted under 35 U.S.C. 154(b) by 0 days.

(21) Appl. No.: 14/513,137

(22) Filed: Oct. 13, 2014

(65) Prior Publication Data

US 2015/0104523 A1    Apr. 16, 2015

Related U.S. Application Data

(60) Provisional application No. 61/890,291, filed on Oct. 13, 2013.

(51) Int. Cl.

| | |
|---|---|
| *A61K 36/00* | (2006.01) |
| *A61K 35/20* | (2006.01) |
| *A61K 36/28* | (2006.01) |
| *A61K 36/79* | (2006.01) |
| *A61K 36/82* | (2006.01) |
| *A61K 36/81* | (2006.01) |
| *A61K 36/9066* | (2006.01) |
| *A61K 36/704* | (2006.01) |
| *A61K 36/67* | (2006.01) |

(52) U.S. Cl.
CPC .............. *A61K 35/20* (2013.01); *A23L 29/00* (2016.08); *A23L 33/105* (2016.08); *A61K 36/28* (2013.01); *A61K 36/67* (2013.01); *A61K 36/704* (2013.01); *A61K 36/79* (2013.01); *A61K 36/81* (2013.01); *A61K 36/82* (2013.01); *A61K 36/9066* (2013.01)

(58) Field of Classification Search
None
See application file for complete search history.

(56) References Cited

U.S. PATENT DOCUMENTS

| | | | |
|---|---|---|---|
| 7,226,625 B2 | 6/2007 | Subbiah | |
| 2003/0026847 A1* | 2/2003 | Lance et al. | 424/579 |
| 2004/0234544 A1* | 11/2004 | Jager | A23L 1/30 424/195.15 |
| 2005/0142124 A1 | 6/2005 | Kaiser | |
| 2008/0081076 A1 | 4/2008 | Lisonbee et al. | |
| 2009/0053197 A1 | 2/2009 | Ramaekers | |
| 2009/0081243 A1 | 3/2009 | Brandon et al. | |
| 2009/0252796 A1 | 10/2009 | Mazed et al. | |
| 2010/0119531 A1 | 5/2010 | Vaughan et al. | |
| 2011/0064720 A1 | 3/2011 | Amato | |
| 2012/0225053 A1 | 9/2012 | Dushenkov et al. | |

FOREIGN PATENT DOCUMENTS

WO    2011/014448 A1    2/2011

OTHER PUBLICATIONS

Sugisawa, A low-molecular-weight fraction of bovine colostrum and milk enhances the oxidative burst activity of polymorphonuclear leukocytes. Veterinary research communications, (Sep. 2003) vol. 27, No. 6, pp. 453-461.*
"4Life Transfer Factor Renuvo." pp. 1-2. Jan. 29, 2014. Retrieved from the Internet: <http://www.4tife.com/images/media/MediaUpload_PpsPdf_20140207102512pdf> on Dec. 12, 2014.
"4Life Transfer Factor Vista," pates 1-27, Dec. 16, 2013. Retrieved from the Internet:<http://online.pubhtm15.com/czip/snwg/snwg.pdf> on Dec. 12, 2014.
Fukui et al., "Mechanism for the Protective Effect of Resveratrol against Oxidative Stress-Induced Neuronal Death," Free Radical Biology & Medicine, Sep. 1, 2010, vol. 49, pp. 800-813.
Joy et al. "The effects of 8 weeks of whey or rice protein supplementation on body composition and exercise performance," Nutrition Journal, Jun. 20, 2013 (Jun. 20, 2013), vol. 12, Issue 86, pp. 1-7.
Kaushai et al. TNF-α and Temporal Changes in Sleep Architecture in Mice Exposed to Sleep Fragmentation, PLoS ONE, Sep. 21, 2012, vol. 7, e45610, pp. 1-17.
United States Patent and Trademark Office, Acting as the International Search Authority, "International Search Report and Written Opinion," mailed Feb. 4, 2015 in international patent application No. PCT/US2014/060309.

* cited by examiner

*Primary Examiner* — Qiuwen Mi
(74) *Attorney, Agent, or Firm* — Durham Jones & Pingar, P.C. Intellectual Property Law Group

(57) ABSTRACT

Therapeutic compositions for addressing physiological stresses and aging include an immune modulator and one or more adaptogenic nutrients. Some non-limiting examples of immune modulators include as transfer factor, low molecular weight fraction immune modulators and/or other low molecular weight fractions of colostrum, egg or any other source of transfer factor or low molecular weight fraction immune modulators. Methods for administering immune modulators and adaptogenic nutrients to a subject to address the effects of physiological stresses and aging in the body of the subject, such as inflammatory responses, are also disclosed.

16 Claims, No Drawings

THERAPEUTIC COMPOSITIONS AND METHODS FOR ADDRESSING PHYSIOLOGICAL STRESSES AND AGING

CROSS-REFERENCE TO RELATED APPLICATION

A claim for the benefit of priority to U.S. Provisional Patent Application No. 61/890,291, filed on Oct. 13, 2013 and titled "THERAPEUTIC COMPOSITIONS AND METHODS FOR ADDRESSING PHYSIOLOGICAL STRESSES" ("the '291 Provisional Application") is hereby made pursuant to 35 U.S.C. §119(e). The entire disclosure of the '291 Provisional Application is hereby incorporated herein.

TECHNICAL FIELD

This disclosure relates generally to therapeutic compositions and methods for addressing physiological stresses and aging. More specifically, therapeutic compositions are disclosed that include an immune modulator, such as transfer factor, a low molecular weight fraction immune modulator and/or another low molecular weight fraction of colostrum, egg or any other source of transfer factor or low molecular weight fraction immune modulators, and one or more adaptogenic nutrients, as are methods for administering immune modulators and adaptogenic nutrients to a subject to address the effects of physiological stresses and aging in the body of the subject.

SUMMARY

In various aspects, the disclosed subject matter relates to compositions and methods for addressing the effects of physiological stress and aging, as characterized by an increase in inflammation in a subject's body and a decrease in the body's detoxifying defenses.

A composition that incorporates teachings of this disclosure may include an immune modulating component and an adaptogenic nutrient component.

Without limitation, the immune modulating component, which is also referred to herein as a "transfer factor component," may comprise transfer factor, a low molecular weight fraction immune modulator of the type disclosed by U.S. Patent Application Publication 2008/0081076 of Lisonbee et al., any other low molecular weight (e.g., 12,000 Da or less) fraction of any source of transfer factor and/or low molecular weight fraction immune modulators (e.g., colostrum, whey, milk, egg, T lymphocytes (from any animal), etc.), any other immune modulator or any combination of immune modulators. Each immune modulator may be obtained from a suitable source, such as a mammalian source animal, an avian source animal, or any other type of animal (e.g., a reptile, an amphibian, etc.). Each immune modulator may be part of an extract that has been obtained from the source animal. Non-limiting examples include extracts of colostrum (from mammalian source animals), eggs (from avian, reptilian, amphibian or fish source animals), blood (from any type of source animal), tissue (e.g., spleen, liver, marrow, etc.—from any type of source animal) or the like.

The adaptogenic nutrient component of various embodiments of the disclosed composition may include one or more adaptogenic nutrients. As used herein, the term "nutrient" includes, but is not limited to, phytonutrients, such as various herbs. A variety of adaptogenic nutrients may be included in a composition according to this disclosure, and may be selected on the basis of their known or potential effects. Various examples of adaptogenic nutrients that may be included in the composition include, but are not limited to, any of the following or, where appropriate, extracts or fractions thereof: *Rhaponticum carthamoides, Schisandra chinensis, Camellia sinensis, Withania somnifera, Curcuma longa, Polygonum cusipadatum, Piper nigrum, Panax quinquefolius, Panax ginseng, Eleutherococcus senticosus, Emblica officinalis, Astragalus membranaceus, Cordyceps sinensis, Codonopsis pilosula, Tinospora cordifolia, Polygonum multiflorum, Ocimum sanctum, Gynostemma pentaphyllum, Glycyrrhiza glabra, Lycium chinense, Pseudostellaria heterophylla, Ganoderma lucidum, Rhodiola rosea, Asparagus racemosus*, shilajit (*Asphaltum punjabianum*), *Takus baccata, Pfaffia paniculata, Vitis vinifera, Silybum marianum, Bacopa monnieri*, colostrum, whey, milk and acetyl-1-carnitine HCl.

In some embodiments, a composition may include an immune modulator component, which is also referred to herein as a transfer factor component, as well as an adaptogenic nutrient component and any of a variety of optional additional ingredients. In other embodiments a composition may consist essentially of the immune modulator component and the adaptogenic nutrient component, with non-essential ingredients including oxcipients, vitamins, minerals and the like. In still other embodiments, the composition may consist of the immune modulator component and the adaptogenic nutrient component.

Together, the immune modulating component and the adaptogenic nutrient component may address one or more of the effects of physiological stress and/or aging. Accordingly, the adaptogenic nutrients that are included in the composition may be selected on the basis of their known or purported ability to address one or more types of physiological stress and/or aging and/or to address one or more of the effects of physiological stress and/or aging. Further, the relative proportions of the ingredients of a composition according to this disclosure may be formulated, or tailored, to provide a desired response to physiological stress and/or aging.

A few examples of physiological stress include the stresses that accompany poor eating habits (e.g., the consumption of foods that are high in fats and/or sugars, etc.), vigorous exercise, overly strenuous or stressful work (e.g., consistently working ten or more hours per day, etc.), lack of sleep, or sleep deprivation (which may vary from individual to individual but, in general, may be considered to include six hours or less sleep per night, on average, etc.), extended travel, exposure to an environmental pollutant, aging, as well as a variety of other factors. As used herein, the terms "vigorous" and "strenuous," as respectively used in conjunction with the terms "exercise" and "work," and in conjunction with other physical activities implies that an individual or a subject has performed an above-normal amount of those activities. As an example, any exercise, including new training programs—even training programs that include typically non-vigorous, typically non-strenuous amounts of exercise—may be considered to be "vigorous" for sedentary, untrained subjects. Increases in the amount, or volume, and intensity of a subject's physical activities, in comparison to the levels of those physical activities to which the subject is accustomed, may also be considered to be "vigorous."

The effects of physiological stress and/or aging may include an increase in inflammation in the body of a subject (which may be accompanied or even caused by a variety of factors, such as an increase (e.g., an acute rise, etc.) in inflammatory signaling, including, without limitation, the expression of tumor necrosis factor-α (TNF-α) in the body of a subject, an increase in protein carbonyls in the subject's body, etc.), a decrease in the body's detoxifying defenses (e.g., a decrease in the expression of mitochondrial superoxide dismutase-2 (SOD-2) in the body of the subject, etc.), an increase in central fat mass in a subject's body and an increase in the overall mass of the subject's body, to name only a few.

In view of the foregoing, a composition may be formulated, or tailored, to: moderate (e.g., reduce, etc.) an inflammatory response by (e.g., an amount of TNF-α, amounts of protein carbonyls, etc., in) a tissue of a subject; moderate (e.g., increase, etc.) a detoxification defense by (e.g., an amount of SOD-2 in) a subject's body; moderate (e.g., slow, reverse, etc.) an increase in central fat stored by the body of the subject; moderate (e.g., slow, reverse, etc.) an increase in body mass; etc.

One or more immune modulators and one or more adaptogenic nutrients may be administered in conjunction with one another to address one or more of the effects of physiological stress and/or aging. Such administration may be provided acutely (e.g., one, two or a few doses over a short period of time; a high dose at a specified frequency (e.g., every four hours, every six hours, every twelve hours, etc.) until an inflammatory response has diminished to an acceptable level, etc.), sub-acutely (e.g., doses over a period of days, etc.) or in a consistent manner over an extended period of time (e.g., daily dosages for a month or longer, etc.). When accompanied by the subject's exposure to physiological stress and/or aging, the immune modulator(s) and adaptogenic nutrient(s) can control one or more of the effects of such stress or support healthy aging. When administered after any physiological stress and/or aging on the subject, the immune modulator(s) and adaptogenic nutrient(s) may reduce one or more of the effects of such stress.

Other aspects, as well as features and advantages of various aspects, of the disclosed subject matter will become apparent to those of ordinary skill in the art through consideration of the ensuing description and the appended claims.

DETAILED DESCRIPTION

A composition according to this disclosure includes an immune modulator component and an adaptogenic nutrient component. The immune modulator component may include one or more immune modulators, such as transfer factor, a low molecular weight fraction immune modulator, any other low molecular weight (e.g., 12,000 Da or less) fraction of any source of transfer factor and/or low molecular weight fraction immune modulators (e.g., colostrum, whey, milk, egg, T lymphocytes (from any animal), etc.), any other immune modulator or any combination of any of the foregoing. The adaptogenic nutrient component may include a synergistic combination of adaptogenic nutrients. In some embodiments, the composition may also include one or more components that enhance a subject's immune system function, cognitive activity, metabolism, endocrine, liver and/or kidney function, sex hormone and/or sexual function, skeletal muscle, cardiorespiratory and/or cardiovascular function, human performance, body composition or the like.

In a specific embodiment, a composition that addresses physiological stress and/or aging and/or their effects includes, consists essentially of or even consists of:

4Life® Transfer Factor Tri-Factor;
*Rhaponticum carthamoides* extract (root);
*Schisandra chinensis* extract (fruit);
ALCAR (as acetyl-1-carnitine HCl);
*Camellia sinensis* (Green Tea) extract (leaf);
*Withania somnifera* (Ashwagandha) extract (root);
Curcuminoids (e.g., as *Curcuma longa* (Turmeric) extract (rhizome), another turmeric extract or from other sources);
Resveratrol (e.g., as *Polygonum cuspidatum* (or extract (e.g., root, etc.) thereof), grape seed (or extract thereof) or from other sources; and
Piperine (e.g., as *Piper nigrum* (black pepper) (or extract (e.g., fruit, etc.) thereof) or from other sources).

The composition may comprise an oral dietary supplement. It may be synergistically formulated to promote a more youthful and healthy response to advanced aging and/or physiological stresses, such as poor dietary habits, vigorous exercise, work (including strenuous work), poor sleeping, aging, exposure to common environmental stressors (e.g., air travel, environmental pollutants, etc.) or any other physiological stress that has negative metabolic and/or biochemical effects. Examples of such negative metabolic and/or biochemical effects include, but are not limited to, an inflammatory response and a reduction in the body's ability to detoxify itself. More specifically, the composition may be formulated to moderate inflammation, detoxification or the like. Even more specifically, the composition may be formulated to reduce the amount of the proinflammatory mediator, TNF-α in the body of a subject, and to increase the body's ability to fight free radicals. Although inflammation is itself a healthy response to a stressful assault on a cell, if responded to improperly or left out of control, the inflammatory effects on a cell (and globally, on a subject's body) can become problematic. For example, advanced aging, fat gain, muscle loss, poor cognitive and sexual function, and many more such events have all been linked to inflammation. By reducing inflammation, the composition may help speed the body's natural recovery and improve the aging process.

The immune modulating component may include transfer factor, a low molecular weight fraction immune modulator of the type disclosed by U.S. Patent Application Publication 2008/0081076 of Lisonbee et al., any other low molecular weight (e.g., 12,000 Da or less) fraction of any source of transfer factor and/or low molecular weight fraction immune modulators (e.g., colostrum, whey, milk, egg, T lymphocytes (from any animal), etc.), any other immune modulator or any combination of immune modulators. Each immune modulator may be obtained from a suitable source, such as a mammalian source animal or an avian source animal. Each immune modulator may be part of an extract or fraction that has been obtained from the source animal. Non-limiting examples include extracts of colostrum (from mammalian source animals), eggs (from avian, reptilian, amphibian or fish source animals), blood (from any type of source animal), tissue (e.g., spleen, liver, marrow, etc.—from any type of source animal) or the like.

The adaptogenic nutrients of various embodiments of the disclosed composition are targeted to support the immune system, and may be body system-specific. Various examples of adaptogenic nutrients that may be included in the composition include, but are not limited to, the following:

*Rhaponticum carthamoides*, which is also known as *Leuzea carthamoides* or Maral root, is a flowering herb native to the alpine and subalpine regions of eastern Siberia, as well as in Mongolia, Kazakhstan and northwest China (Xingjiang province). *R. carthamoides* is an approved adaptogen—a natural substance that is nontoxic, helps the body adapt to stress and/or aging, and has a normalizing effect on the body, helps to restore balance, and supports normal metabolic function—and therefore is generally recognized as supporting a wide array of body system functions. *R. carthamoides* may be included in the composition because of its adaptogenic herb classification and its previously reported effects on inflammation. Synergistically, *R. carthamoides* may be included in the composition to support immune function and promote healthy aging via its reported effects on muscle mass, adrenal function and sexual health, which affect recovery, energy and vitality;

*Schisandra chinensis*, which is also known as *Kadsura chinensis* or Magnolia vine, is an herb native to several Chinese provinces and is an approved adaptogen—a natural substance that is nontoxic, helps the body adapt to stress and/or aging, and has a normalizing effect on the body, helps to restore balance, and supports normal metabolic function—and therefore is generally recognized as supporting a wide array of body system functions. *S. chinensis* may be included in the composition because of its adaptogenic herb classification and its previously reported effects on inflammation. Synergistically, *S. chinensis* may be included in the composition to support immune function and promote healthy aging via its reported effects on liver, kidney and adrenal function and sexual health, which affect metabolism, mood, energy, recovery and vitality;

ALCAR (as acetyl-1-carnitine HCl) is a naturally occurring derivative of the amino acid, L-carnitine. ALCAR is naturally produced within the body, primarily within cell mitochondria (primary energy-producing region of a cell) and peroxisomes (primary fat oxidation region of a cell). Mitochondrial density within a cell affects a cell's ability to utilize oxygen and produce energy, and a decrease in mitochondrial density contributes to accelerated aging. ALCAR may be included in the composition because of its previously reported effects on inflammation, and ability to reduce the amount of TNF-α in a body of a subject and to increase the amount of SOD2 in the body of the subject. Synergistically, ALCAR may be included in the composition to support immune function and promote healthy aging via its reported effects on brain and mitochondrial function, and skeletal muscle and cardiovascular health, which affect energy and metabolism;

*Camellia sinensis*, which is also known as green tea, is widely cultivated but native to tropical and temperate regions of Asia (e.g., China, India, and Indo-China) and has a long history of human use. *C. sinensis* may be included in the composition for its previously reported effects on inflammation, and ability to reduce TNF-α and increase SOD2. Synergistically, *C. sinensis* may be included in the composition to support immune function and promote healthy aging via its reported effects on a wide array of body systems, which affect mood, energy, metabolism, recovery, and vitality;

*Withania somnifera* (ashwagandha), which is also known as *Physalis somnifera* or winter cherry, is native to the somewhat drier sub-tropic regions of India, Pakistan, Sri Lanka and parts of Africa. *W. somnifera* is an approved adaptogen. Therefore, *W. somnifera* is generally recognized as supporting a wide array of body system functions. *W. somnifera* may be included in the composition because of its adaptogenic herb classification and its previously reported effects on inflammation. Synergistically, *W. somnifera* may be included in the composition to support immune function and promote healthy aging via its reported effects on adrenal function, sexual health and muscle, which affect recovery, mood and vitality;

*Curcuma longa* extract (rhizome), which is also known as turmeric, is a member of the ginger family and is a perennial shrub native to southern Asia and widely cultivated in India, China, Taiwan, Japan, Burma, Indonesia and throughout Africa. Turmeric and other curcuminoids have a long history of use, most notably as digestive aids. *C. longa* or another suitable source of curcuminoids may be included in the composition for its curcuminoid active concentration, as curcumnoids are known to provide beneficial effects on inflammation, on reducing TNF-α and on increasing SOD2. Synergistically, curcuminoids may be included in the composition to support immune function and promote healthy aging via its reported effects on a wide array of body systems, which affect mood, energy, metabolism, recovery and vitality;

*Polygonum cuspidatum*, which is also known as Japanese knotweed, is a perennial plant native to eastern Asia, in Japan, China and Korea. *P. cuspidatum* or any other suitable source of resveratrol may be included in the composition for its resveratrol active concentration. Resveratrol is known to provide beneficial effects on inflammation, and on reducing TNF-α and increasing SOD2. Synergistically, resveratrol may be included in the composition to support immune function and promote healthy aging via its reported effects on a wide array of body systems, which affect mood, energy, metabolism, recovery and vitality; and

*Piper nigrum*, which is also known as black pepper, is a tropical plant native to southern India and Sri Lanka. Black pepper and other sources of piperine have a long history of use, most notably as a food additives and digestive aids. *P. nigrum* or any other suitable source of piperine may be included in the composition for having a piperine active concentration that provides beneficial effects on inflammation, and on reducing TNF-α and increasing SOD2. Synergistically, piperine may be included in the composition to support immune function and promote healthy aging via its reported effects on a wide array of body systems, which affect mood, energy, metabolism, recovery and vitality.

A composition according to this disclosure may be administered in any of a variety of ways. As an alternative to administering a composition that includes an immune modulating component and an adaptogenic nutrient component, an immune modulator and a blend of adaptogenic nutrients may be administered to the subject. For the sake of simplicity, both the composition and the separate components are referred to hereinafter as a composition. As a non-limiting example, one serving of the composition may be administered twice each day, on an empty stomach first thing in the morning and again about six hours to about eight hours later. As another non-limiting example, a subject may take three or four servings of the composition each day, particularly when the subject is subjected or will be subjected to an above-normal amount of physiological stress (e.g., before exercise, immediately after exercise, while traveling, etc.). The composition may be administered with one or more other nutritional supplements (e.g., 4LIFE® TRANSFER FACTOR®, a multivitamin, fish oil and/or a probiotic, etc.).

EXAMPLE COMPOSITION

A specific embodiment of the composition includes, consists essentially of or consists of the following ingredients in one or more of the per serving amounts listed below:

4Life® TRANSFER FACTOR® TRI-FACTOR® (25 mg to 500 mg; about 25 mg; about 50 mg; about 75 mg; about 100 mg; about 150 mg; about 250 mg; etc.);

*Rhaponticum carthamoides* extract (root) (≥5% total ecdysteroids) (50 mg to 2,000 mg; 200 mg to 300 mg; about 200 mg; about 225 mg; about 250 mg; about 275 mg; about 300 mg; about 500 mg; etc.);

*Schisandra chinensis* extract (fruit) (≥2% total schisandrins) (50 mg to 2,000 mg; 200 mg to 300 mg; about 200 mg; about 225 mg; about 250 mg; about 275 mg; about 300 mg; about 500 mg; etc.);

ALCAR (as acetyl-1-carnitine HCl) (50 mg to 2,000 mg; 200 mg to 300 mg; about 200 mg; about 225 mg; about 250 mg; about 275 mg; about 300 mg; about 500 mg; etc.);

*Camellia sinensis* (green tea) extract (leaf) (≥45% EGCG) (25 mg to 2,000 mg; 200 mg to 300 mg; about 200 mg; about 225 mg; about 250 mg; about 275 mg; about 300 mg; about 500 mg; etc.);

*Withania somnifera* (ashwagandha) extract (root) (≥5% total with anolides) (25 mg to 500 mg; about 25 mg; about 50 mg; about 75 mg; about 100 mg; about 150 mg; about 250 mg; etc.);

*Curcuma longa* (turmeric) extract (rhizome) (≥95% curcuminoids) (10 mg to 500 mg; about 25 mg; about 50 mg; about 75 mg; about 100 mg; about 150 mg; about 250 mg; etc.);

*Polygonum cuspidatum* extract (root) (≥50% resveratrol) (5 mg to 500 mg; about 25 mg; about 50 mg; about 75 mg; about 100 mg; about 150 mg; about 250 mg; etc.); and

*Piper nigrum* (black pepper) extract (fruit) (≥95% piperine) (2.5 mg to 500 mg; about 25 mg; about 50 mg; about 75 mg; about 100 mg; about 150 mg; about 250 mg; etc.).

EXAMPLE

As an example of its potential efficacy in addressing effects of physiologic stress and/or aging, a composition according to this disclosure was administered to adult rodents in a recent randomized, placebo-controlled, linearly designed safety and efficacy study, conducted at the University of Missouri, Department of Biomedical Sciences (Columbia, Mo.) and in collaboration with Auburn University Department of Kinesiology (Auburn, Ala.). The human equivalent of two (2) servings per day of an EXAMPLE COMPOSITION was administered to each adult rodent of a test group for 30 days, and was demonstrated to significantly reduce the adverse effects observed in response to a typical inflammation-inducing Westernized diet (high-fat, high-sugar). Specifically, the EXAMPLE COMPOSITION significantly reduced the inflammatory response to a Westernized diet by 64% (measured as tumor necrosis factor-alpha, or TNF-α expression). The EXAMPLE COMPOSITION also provided a 42% reduction in the oxidative damage caused to cellular proteins (measured as protein carbonyl concentration) and a 43% increase in the detoxifying enzyme responsible for reducing the damage caused by free radicals (measured as mitochondrial superoxide dismutase-2, or SOD2). The EXAMPLE COMPOSITION plus a Westernized diet even resulted in a 57% lower inflammatory response than just consuming a healthy low-fat, low-sugar control diet alone. The EXAMPLE COMPOSITION plus a Westernized diet significantly reduced the oxidative damage to cellular proteins by 53%, and increased the presence of detoxifying SOD2 by over 74% versus a healthy control diet only group. Additionally, a Westernized diet plus the EXAMPLE COMPOSITION significantly reduced the accumulation of central (or visceral) fat mass by 6% and body mass by 95% versus the unhealthy diet treatment alone. Blood chemistry and liver histopathology data also revealed that the human equivalent of two servings per day of the EXAMPLE COMPOSITION for 30 days, presents no signs of adverse safety.

Some of these results are set forth in the following table:

| SERVING SIZE | SERVINGS per DAY | STRUCTURE-FUNCTION CLAIMS* | DOSE OF SUBSTANTIATED ACTIVE INGREDIENT(S) | REFERENCE(s) |
| --- | --- | --- | --- | --- |
| 2 caps | 2 | A high-fat, high-sugar inflammatory diet + an EXAMPLE COMPOSITION resulted in a significant decrease in liver TNF-α (−64%) versus a high-fat, high-sugar diet alone<br>A high-fat, high-sugar inflammatory diet + an EXAMPLE COMPOSITION resulted in a 43% increase in liver mitochondria SOD2 versus a high-fat, high-sugar diet alone<br>A high-fat, high-sugar inflammatory diet + an EXAMPLE COMPOSITION resulted in reduced liver Protein Carbonyls (−42%) versus a high-fat, high-sugar diet alone<br>A high-fat, high-sugar inflammatory diet + an EXAMPLE COMPOSITION resulted in a significantly reduced increase in Central (or Visceral) Fat Mass (−6%) versus a high-fat, high-sugar diet alone<br>A high-fat, high-sugar inflammatory diet + an EXAMPLE COMPOSITION resulted in a significantly reduced increase in Body Mass (−95%) versus a high-fat, high-sugar diet alone<br>A high-fat, high-sugar inflammatory diet + an EXAMPLE COMPOSITION resulted in a 57% decrease in liver TNF-α versus a healthy control diet alone<br>A high-fat, high-sugar inflammatory diet + an EXAMPLE COMPOSITION resulted in a 53% decrease in the presence of liver Protein Carbonyls versus a healthy control diet alone<br>A high-fat, high-sugar inflammatory diet + an EXAMPLE COMPOSITION resulted in a 74% increase in liver mitochondria SOD2 versus a healthy control diet alone<br>Research evidence suggests that an EXAMPLE COMPOSITION may decrease the inflammatory response to an unhealthy diet by as much as 64% | 2 servings per day ×30 days of an EXAMPLE COMPOSITION (Human dose equivalent; study in adult rats) | Mobley, C.B., et al, "Effects of herbal adaptogens combined with protein fractions from bovine colostrums and hen egg yolk on markers of inflammation, liver health, and antioxidant status following high fat/high sucrose diet feeding in rats," *Nutr. Metab.* (2014) (In review). |

-continued

| SERVING SIZE | SERVINGS per DAY | STRUCTURE-FUNCTION CLAIMS* | DOSE OF SUBSTANTIATED ACTIVE INGREDIENT(S) | REFERENCE(s) |
|---|---|---|---|---|
| | | Research evidence suggests that an EXAMPLE COMPOSITION may increase the body's detoxifying defenses in response to an unhealthy diet by as much as 74% | | |
| | | Research evidence suggests that an EXAMPLE COMPOSITION may decrease the oxidative damage caused by an unhealthy diet by as much as 42% | | |
| | | Research evidence suggests that an EXAMPLE COMPOSITION may decrease the inflammatory response to a typical stress by as much as 64% | | |
| | | Research evidence suggests that an EXAMPLE COMPOSITION may increase the body's detoxifying defenses in response to a typical stress by as much as 74% | | |
| | | Research evidence suggests that an EXAMPLE COMPOSITION may decrease the oxidative damage caused by a typical stress by as much as 42% | | |
| | | Research evidence suggests that an EXAMPLE COMPOSITION does not cause any adverse events or possess any serious safety risks when used as directed for 30 days | | |

*Claims are additive; claims are not repeated as the number of "Servings Per Day" increases Although the foregoing description sets forth many specifics, these should not be construed as limiting the scope of any of the claims, but merely as providing illustrations of some embodiments and variations of elements or features of the disclosed subject matter. Other embodiments of the disclosed subject matter may be devised which do not depart from the spirit or scope of any of the claims. Features from different embodiments may be employed in combination. Accordingly, the scope of each claim is limited only by its plain language and the legal equivalents thereto.

What is claimed is:

1. A method for addressing an inflammatory response by a body of a subject to a physiological stress, comprising:
    subjecting a body of a subject to a physiological stress that causes an increase in an inflammatory response by the body; and
    within a predetermined period of time before, during or within a predetermined period of time after subjecting the body of the subject to the physiological stress, administering an immune modulator and a blend of adaptogenic nutrient components to the subject, the blend of adaptogenic nutrient components consisting essentially of Rhaponticum carthamoides extract, Schisandra chinensis extract, acetyl-1-carnitine HCl, Camellia sinensis extract Withania somnifera extract, a source of a curcuminoid, a source of resveratrol, and a source of piperine, the immune modulator and the blend of adaptogenic nutrient components moderating the inflammatory response by the body of the subject.

2. The method of claim 1, wherein subjecting the body of the subject to the physiological stress comprises subjecting the body of the subject to at least one of an inflammatory diet, strenuous work hours, vigorous exercise, sleep deprivation, extended travel, aging or an environmental pollutant.

3. The method of claim 1, wherein administering is effected over a period of at least one month and further includes moderating a central fat mass of the body of the subject.

4. The method of claim 1, wherein administering is effected over a period of at least one month and further includes moderating a body mass of the body of the subject.

5. The method of claim 1, wherein administering is effected acutely.

6. The method of claim 1, wherein:
    subjecting comprises increasing an amount of at least one of tumor necrosis factor-α and protein carbonyls in the body of the subject; and
    administering includes moderating an amount of at least one of the tumor necrosis factor-α and protein carbonyls in the body of the subject.

7. The method of claim 6, wherein moderating includes decreasing the amount of at least one of tumor necrosis factor-α and protein carbonyls in the body of the subject.

8. The method of claim 1, wherein administering further includes administering a low molecular weight fraction immune modulator to the subject.

9. A method for addressing an inflammatory response by a body of a subject to a physiological stress or as a characteristic of advanced aging, comprising:
    subjecting a body of a subject to a physiological stress that causes a decrease in a detoxifying defense by the body; and
    within a predetermined period of time before, during or within a predetermined period of time after subjecting the body of the subject to the physiological stress, administering an immune modulator and a blend of adaptogenic nutrient components to the subject, the blend of adaptogenic nutrient components consisting essentially of Rhaponticum carthamoides extract, Schisandra chinensis extract, acetyl-1-carnitine HCl, Camellia sinensis extract, Withania somnifera extract, a source of a curcuminoid, a source of resveratrol, and a source of pipeline the immune modulator and the blend of adaptogenic nutrient components moderating the detoxifying defense by the body of the subject.

10. The method of claim 9, wherein:
    subjecting comprises decreasing an amount of mitochondrial superoxide dismutase-2 in the body of the subject; and
    administering comprises moderating the amount of mitochondrial superoxide dismutase-2 in the body of the subject.

11. The method of claim 10, wherein moderating includes increasing the amount of mitochondrial superoxide dismutase-2 in the body of the subject.

12. The method of claim 9, wherein administering further includes administering a low molecular weight fraction immune modulator to the subject.

13. A method for addressing an inflammatory response by a body of a subject to a physiological stress, comprising:
   subjecting a body of a subject to a physiological stress that causes an increase in an inflammatory response by the body; and
   within a predetermined period of time before, during or within a predetermined period of time after subjecting the body of the subject to the physiological stress, administering an immune modulator and a blend of adaptogenic nutrient components to the subject, the immune modulator comprising a source of transfer factor, the blend of adaptogenic nutrient components consisting essentially of *Rhaponticum carthamoides* extract *Schisandra chinensis* extract, acetyl-1-carnitine HCl, *Camellia sinensis* extract, *Withania somnifera* extract, a source of a curcuminoid, a source of resveratrol, and a source of piperine, the immune modulator and the blend of adaptogenic nutrient components moderating the inflammatory response by the body of the subject.

14. The method of claim 13, wherein administering comprises administering a 12,000 D or less fraction of the immune modulator to the subject.

15. The method of claim 13, wherein administering comprises administering an immune modulator comprising colostrum to the subject.

16. The method of claim 13, wherein administering comprises administering an immune modulator comprising avian egg to the subject.

* * * * *